US008473308B2

(12) United States Patent
Fackler et al.

(10) Patent No.: US 8,473,308 B2
(45) Date of Patent: Jun. 25, 2013

(54) SYSTEM AND METHOD FOR SHARING MEDICAL INFORMATION

(76) Inventors: James Fackler, Baltimore, MD (US); Jean Francois Lancelot, San Diego, CA (US)

( * ) Notice: Subject to any disclaimer, the term of this patent is extended or adjusted under 35 U.S.C. 154(b) by 37 days.

(21) Appl. No.: 13/062,631

(22) PCT Filed: Jul. 15, 2009

(86) PCT No.: PCT/US2009/050676
§ 371 (c)(1),
(2), (4) Date: May 23, 2011

(87) PCT Pub. No.: WO2010/030432
PCT Pub. Date: Mar. 18, 2010

(65) Prior Publication Data
US 2011/0225002 A1 Sep. 15, 2011

Related U.S. Application Data

(60) Provisional application No. 61/095,503, filed on Sep. 9, 2008.

(51) Int. Cl.
*G06Q 50/00* (2012.01)
(52) U.S. Cl.
USPC .......................................................... 705/2
(58) Field of Classification Search
USPC .......................................................... 705/2
See application file for complete search history.

(56) References Cited

U.S. PATENT DOCUMENTS

| 6,529,195 | B1 | 3/2003 | Eberlein |
| 6,856,315 | B2 | 2/2005 | Eberlein |
| 7,076,437 | B1 | 7/2006 | Levy |
| 2003/0055679 | A1 | 3/2003 | Soll et al. |
| 2007/0260492 | A1 | 11/2007 | Feied et al. |
| 2008/0052124 | A1 | 2/2008 | Goodman et al. |
| 2009/0144089 | A1 | 6/2009 | Heywood et al. |
| 2010/0245358 | A1 | 9/2010 | Heywood et al. |
| 2012/0084370 | A1 | 4/2012 | Heywood et al. |

OTHER PUBLICATIONS

International Search Report issued in International Application No. PCT/US09/50676, mailed Aug. 25, 2009.
Written Opinion issued in International Application No. PCT/US09/50676, mailed Aug. 25, 2009.
International Preliminary Report on patentability issued in International Application No. PCT/US09/50676, mailed Mar. 24, 2011.
www.patientslikeme.com, printed on Dec. 28, 2012 from web.archive.org archived on Jun. 4, 2009 (1 page).
www.pkc.com, printed on Dec. 28, 2012 from web.archive.org archived on Mar. 16, 2009 (8 pages).
Lawrence L. Weed, "Medical Records that Guide and Teach", The New England Journal of Medicine, vol. 278, No. 11, pp. 593-600, Mar. 14, 1968.
Lawrence L. Weed, "Medical Records that Guide and Teach (Concluded)", The New England Journal of Medicine, vol. 278, No. 12, pp. 652-657, Mar. 21, 1968.
Lawrence L. Weed, "Knowledge Coupling, Medical Education and Patient Care", Critical Review in Medical Informatics, vol. 1, No. 1, pp. 55-79, (1986).

*Primary Examiner* — John Pauls
(74) *Attorney, Agent, or Firm* — DLA Piper LLP US (57) ABSTRACT

A system and method for sharing information, comprising: creating at least one problem-oriented record utilizing at least one modifier to describe at least one attribute of at least one problem; and utilizing the at least one problem-oriented record to share information.

16 Claims, 7 Drawing Sheets

Cognitive Activity Key Points Pattern Recognition
Two distinct types of pattern recognition seen were:
1. Patterns as "templates", and
2. Patterns as real-time merging of template "fragments". Situation analysis at both strategic and tactical levels
Situation analysis occurred on two distinct planes:
1. A strategic level done primarily by attending physicians when attempting to prioritize resource allocation and,
2. A tactical level done primarily by the house staff working rigorously through their tasks. Uncertainty management
Several strategies intensivists use to manage uncertainty are (but not limited to):
1. Acting on the environment to gain more information (e.g., examining a patient's response to therapy)
2. Narrowing diagnostic options / possibilities
3. Using differing organizing frameworks to make sense of patient data (organ view versus problem view
4. Tolerating and living with the uncertainty for a period of time until new or different data is available Creation of "stories" for organization and transfer of patient data.
We observed ICU practitioners using "story-" or "picture" creation as a cognitive strategy to help them tie various pieces of patient data together into a meaningful whole.
These stories provide the ICU team with an organizing mechanism to make decisions about patient care and treatment, and to transfer their understanding of a patient from one care provider to the next. Team Coordination
Team coordination relevant cognitive tasks, in which problems were most often observed, fell into the general categories of:
1. Team Communication.
2. Fragmentary Teams
3. Shifting Teams
4. Increasing numbers of Shift Hand-offs
5. Role Ambiguity in the ICU.
6. External Collaborators in Critical Care.
Little organized attention was observed to the aspects of coordination within the ICU team as well as between the ICU team and others.

SYSTEM AND METHOD FOR SHARING MEDICAL INFORMATION

This application claims priority to provisional application 61/095,503, filed Sep. 9, 2008, which is herein incorporated by reference.

BRIEF DESCRIPTION OF THE DRAWINGS

FIG. 5 illustrates an example of cognitive activity pattern recognition, according to an embodiment.

DETAILED DESCRIPTION

Figure 1:
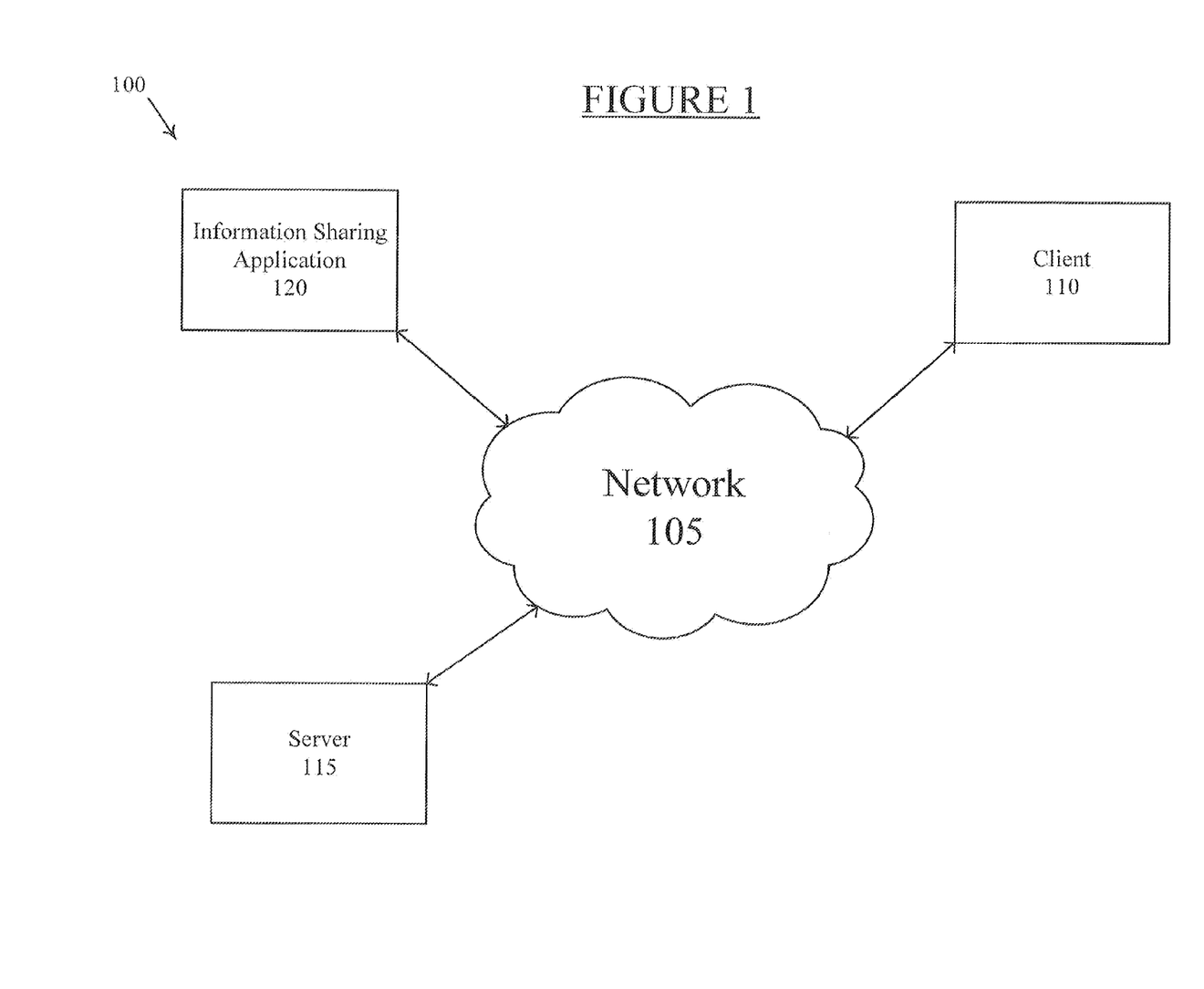
FIG. 1 illustrates a system for sharing medical information, according to an embodiment.

FIG. 1 illustrates a system for sharing medical information, according to one embodiment. The system 100 includes at least one client 110 connected to at least one server 115 through at least one network 105. At least one information sharing application 120 is also connected to the at least one client 110 and the at least one server 115 through the at least one network 105. To help facilitate the sharing, problem-oriented medical records can be created utilizing modifiers to describe attributes of medical problems (e.g., specific medical problems, multiple problems, clusters of problems). The problem-oriented medical records can then be utilized to share information and perform problem-based pattern matching. The system 100 can be used by providers (e.g., doctors, laboratories, care management assistants) and/or patients (and their family and friends) to analyze and compare clinical practice and provide information.

The information sharing application 120 can have compatibility with other IT systems. It can be embeddable in a variety of different portal and other software products, and it can also be used as a stand alone tool. It can require few connections to a healthcare system's core IT infrastructure and its architecture can be generalized and independent of feeder systems. The information sharing application 120 can be made up of web-based components which can be embedded in portals or other applications. The information sharing application 120 can allow external knowledge sources (Isabel (www.isabel-healthcare.com/home/default), Problem Knowledge Couplers (www.pkc.com)) to be linked in for additional decision support.

At least one interface for the information sharing application 120 can be provided on the client 110 and the server 115 so that the providers and/or the patients can access the system 100. The interface can allow full but secure access to the patient problem information and the knowledge bases contained in the system. Of course, the interface can also allow lesser degrees of access, if desirable. In one embodiment, several interfaces can be provided (e.g., graphical, tabular, mind map, timeline, etc.), which can be selected dynamically per user preference for different visual presentations of data (e.g., patient's longitudinal problem list, a particular episode list).

Figure 2:
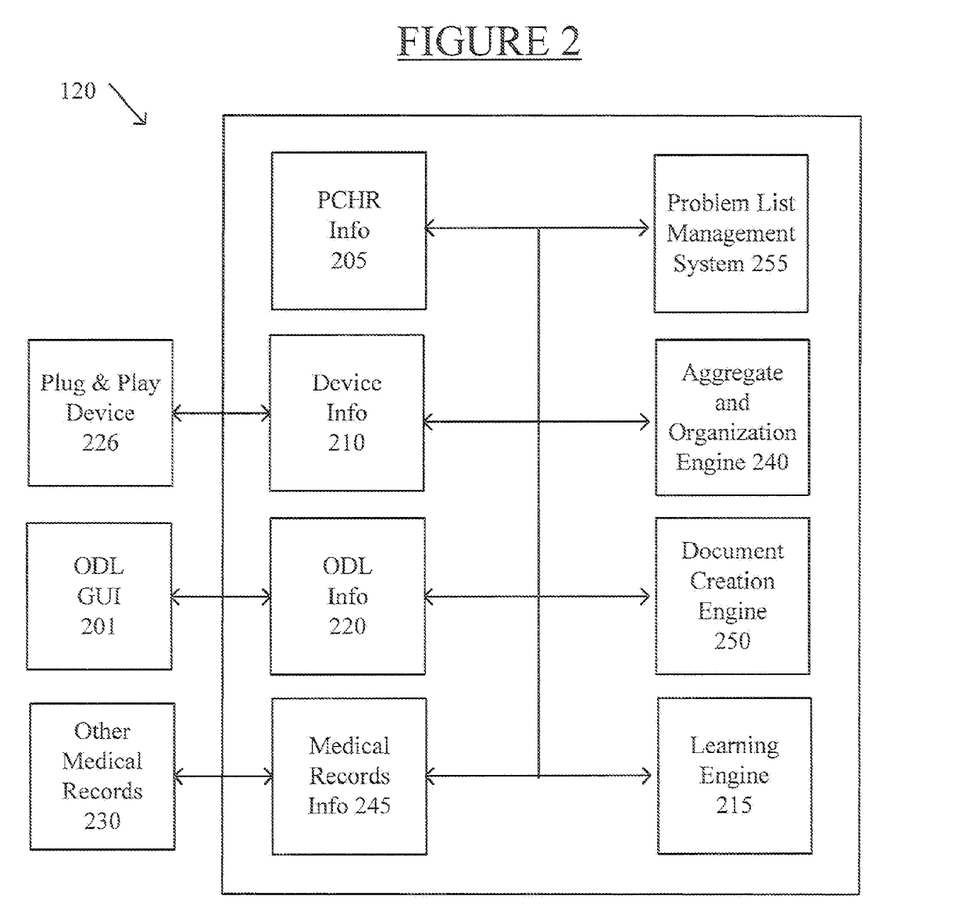
FIG. 2 illustrates an information sharing application, according to an embodiment.

FIG. 2 illustrates details of the at least one information sharing application 120, according to one embodiment. The information sharing application 120 can comprise or interact with other modules, decision support tools, and documents. For example, information can be retrieved, collected, stored, and displayed.

The information sharing application 120 can comprise personally controlled health record (PCHR) information 205 for patients. The PCHR information 205 can include problem-oriented medical records created utilizing modifiers to describe attributes of medical problems (e.g., specific medical problems, multiple problems, clusters of problems). The problem-oriented medical records can then be utilized to share information and perform problem-based pattern matching. PCHR information 205 is described in more detail below.

The PCHR information 205 can be linked to at least one problem list management system 255 that can store the problem list information and keep track of changes made to the problem information. In one embodiment, the problem list management system 255 can invite a user to indicate the reasons why a particular problem is created, resolved, and/or reprioritized, including the source finding(s) or observation(s) which the user feels is causing the problem. Examples of how the problem list management system 255 can help a user include: creating a new problem based on observational inputs; resolve a new problem based on observational inputs; re-parent or otherwise change a problem's position in the patient's problem hierarchy; confirm an existing problem and/or modify its severity based on observational inputs; or rule out a potential problem based on observational inputs; or any combination thereof. The problem list management system 255 can also capture bookkeeping information such as the time and date of each problem information change, or any new or changed relationship between a problem and an observational input, and the identification of the user who made such changes. The problem list management system 255 can also maintain observation observer settings (e.g., using observations of daily living (ODL) information 220 described below) that can prompt the user when new instances of observational inputs (e.g., lab results, vital signs, assessment or physical exam findings, study or diagnostic interpretation, consultation report) are received and invite the user to revise the problem list per his/her clinical judgment. The problem list management system 255 can allow the user to define the relationship of observational inputs to problems in the problem list (e.g., as confirmatory, eliminating or resolving). Observational inputs can also be tagged as "non-pertinent to any problem". The problem list management system 255 can use the associations between problems and observational inputs, the evolution of the problem list hierarchy, and the associated bookkeeping information for the selected patient encounter as inputs to progress notes. The problem list management system 255 can remember the last time a progress note was generated and construct the next progress note by considering all problem changes since the previous progress note's time. If not progress note was created, all problem changes can be considered. The user can also manually choose the beginning and end time within which to consider problem changes.

The information sharing application 120 can also include a aggregation and organization engine 240 that can aggregate all of the information received from the PCHR information 205, organize it (e.g., by problem), and display the data to support a common understanding between the patients and providers. Thus, medical providers looking for patterns in data can search symptoms, signs and supporting data to help reach their decisions. The aggregation and organization engine 240 can collect, retrieve, display, and/or deliver decision support in a problem-oriented fashion. The information sharing application 120 can also create support structures so a PCHR is available to all similar patients (e.g., all MD patients) regardless of their technological access or expertise.

The information sharing application 120 can also include at least one document creation engine 250. Documents related to the patient's problems (e.g., evolution of discovery, resolution, prioritization, and interrelations) can be automatically generated based on the problem-oriented medical records.

In addition, at least one learning engine 245 can be utilized to provide contextual choices given a clinical context. The clinical context can include the patient's existing set of problems, the clinical observations for a current encounter, baseline clinical observations, a user's discipline, specialty, sub-specialty, etc. This can help make the information sharing application 120 easier to use because smaller choice lists can be presented by focusing on current context (e.g., customization to the user). In addition, guidance in using the information sharing application 120 can be better because the user can be invited to consider all the choices available to the user in the user's context, instead of just the choices the user thinks of. The learning engine 245 can also enable retrospective validation or evidence based medicine because it can represent actual clinical usage/associations on actual patients by actual users in an actual care setting. This can help branding (e.g., John Hopkins' practice patterns), restrictions to constrain information (e.g., to certain persons, facilities, disciplines), and benchmarking (e.g., against other providers or institutions, reference institutions, statistical organizations).

The medical records information 215 can include traditional medical provider information (e.g., doctor's records, hospital's records). In addition, information can be accessed or compiled from multiple parties and made available to multiple parties (e.g., home, rehabilitation, acute, and/or critical care parties). The medical record information 215 can be connected to other medical record database(s) 230 so that medical record information can be shared. Existing medical vocabularies (e.g., SNOMED, ICD-9 and/or 10, LOINC, NANDA) can be utilized in some embodiments. Necessary extensions to existing medical vocabularies can also be utilized. In addition, customized vocabularies can be used.

The device information 210 can be connected to at least one plug and play device/system 225 that collects data from at least one device. The device information 210 can collect data from various devices (e.g., keyboard, stylus and/or handwritten recognition, voice), which can stream the data to trained central observers, which can analyze data from physiological monitors, medical devices, and ODL information 220 to discover patterns in home therapy treatments and draw conclusions about current therapies. The device information object can identify patterns of data that flag clinically significant events and trends requiring immediate intervention. In addition, the device information can identify patterns of data that suggest improvements in conditions that warrant analysis and knowledge transfer to the wider communities. All of this can lead to a greater understanding in patient responses to therapy which will enable providers to discover and propagate the most effective therapies with patient advocacy.

A specific medical device can be linked to a specific patient. In one embodiment, the application 120 can have bi-directional data communication capability to support complete and accurate data acquisition from vital signs monitors, infusion pumps, ventilators, portable imaging systems, and other hospital and home-based high-acuity medical devices. This can help enable the development of remote monitoring, advanced clinical decision support systems, intelligent alarms, and robust databases for continuous quality improvement. The routine collection of data from medical devices located within the home, mobile, and hospital-based areas into a PCHR can happen, in one embodiment, using an input-output port with a standard connection (e.g. like the USB) to each device, the input-output port communicating with standard metadata and primary data structures.

Additional information on the PCHR information 205 and observations of daily living (ODL) information 220 is discussed in more detail below.

PCHR. The PCHR information 205 can include medical record information 245 (traditional medical provider information (e.g., doctor's records, hospital's records), laboratory information, other testing information), device information 210 (e.g., physiological monitor information, therapeutic medical device information), and patient and family/friend/assistant recorded current conditions and ODL information 220.

The PCHR information 205 can comprise problem-oriented medical records to organize patient data according to patient's medical problems. The PCHR information 205 can be organized the way patients think about themselves as having symptoms or problems that demand attention. Patients need a problem-oriented set of views into their health and illness information. Metadata structures can be used to store and analyze a patient's problems and subsequently analyze populations of patients with similar medical conditions. The metadata can go beyond a problem name plus onset and resolution dates.

Figure 4:
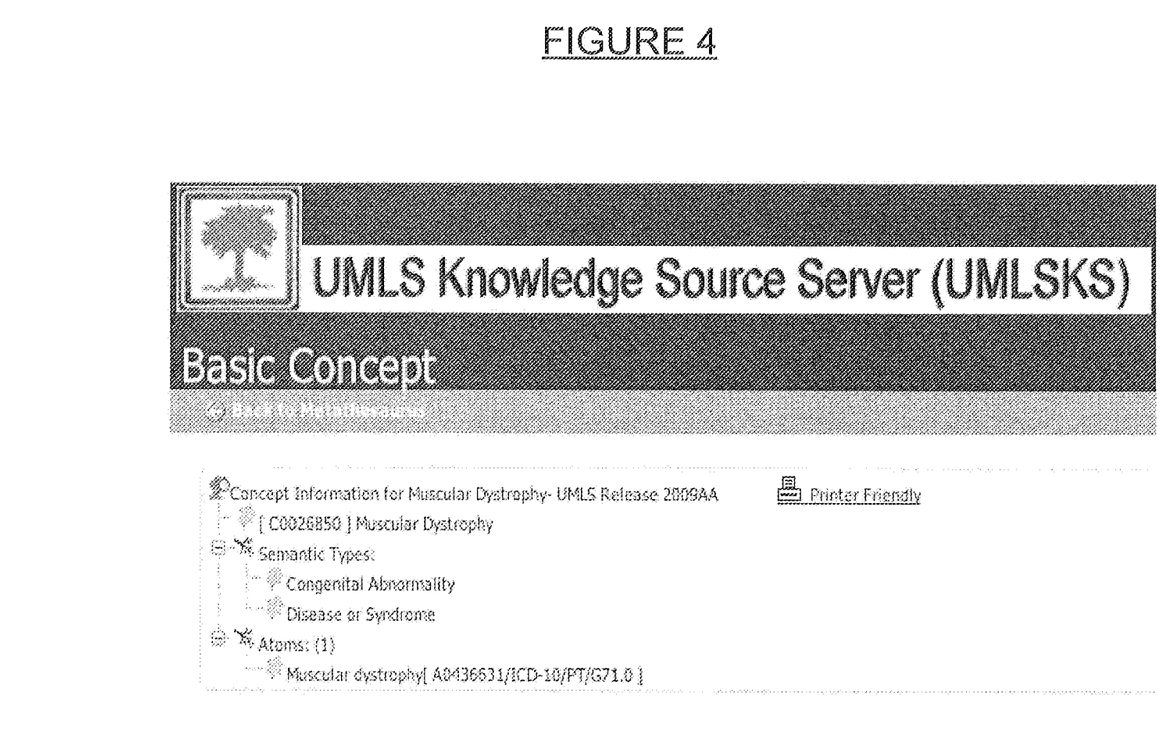
FIG. 4 is an example screen shot, according to an embodiment.

The metadata in the PCHR information 205 can, for example, build on the existing work of the Unified Medical Language System (UMLS) created and maintained in the public domain by the National Library of Medicine within the National Institutes of Health. (It should, however, be noted that other systems can be utilized.) UMLS contains about 1.3 million unique concepts that map about 6.2 million terms within its 126 vocabularies. UMLS also supports a semantic network that maps the unique concepts into 135 broad subject categories or semantic types, and adds 54 semantic relationships between the semantic types. For instance "sign or symptom" is a semantic type and "precedes"' is a semantic relationship. For example, "excess oral secretions" precedes the "disease or syndrome" pneumonia. An example screen-shot querying UMLS for muscular dystrophy in ICD-10 is shown in FIG. 4.

The problem-oriented medical records in the PCHR information 205 can include modifiers. The modifiers can be used to describe attributes of medical problems (e.g., specific medical problems, multiple problems, clusters of problems). Attributes can include: name, synonym, relationship, time stamp, or any combination thereof. The following data model is one example of how a patient's problems can be represented:

DATA MODEL TO REPRESENT PATIENT PROBLEMS

A. Attribution
  a. Person
  b. Patient
  c. Self
  d. Relative
  e. Other observer B. Provider
  a. Provider type
  b. Provider "sub-type"
  c. # of times provider as used the problem
  d. Some Auto-populate
  e. Event trigger based
  f. Data trigger based
  g. Date of addition
C. Categorical
  a. Constitutional
  b. Psych
  c. Social
  d. Neurological
  e. Respiratory
  f. Cardiac
  g. Renal
  h. Hepatic
  i. Toxicological
  j. GI
  k. Nutrition
  l. Hematologic
  m. Infectious
  n. Musculoskeletal
  o. Dermatologic
  p. Ophthalmologic
D. Certainty
  a. Based on individual's guess
  b. Based on algorithm estimates
E. Supporting data
  a. Demographic data
  b. Personal Preferences
  c. Social context
  d. Symptoms
  e. Signs
  f. Lab data
  g. Images
  h. Professional opinions
F. Contradicting data
  a. Demographic data
  b. Personal preferences
  c. Social context
  d. Symptoms
  e. Signs
  f. Lab Data
  g. Images
  h. Professional opinions
G. Related data
  a. From EMR
  b. Other problems
  C. Visits
  d. Therapies
    i. Medications
    ii. May be cause of (i.e. a side effect)
    iii. May be treatment for
  e. Durable devices
  f. Documents
  g. From medical literature
  h. From the web
  i. For professionals
  j. For patients
  k. For families
  l. From database of other patients with the same problem(s)
H. Onset
  a. Hard
  b. Fuzzy
  c. Auto-expiration
I. Resolution
  a. Hard
  b. Fuzzy
  c. Never (i.e. chronic)
  d. Morph
    i. Hard
    ii. Fuzzy
J. Relationship to other problems
  a. Caused by
  b. Result of
  c. Exacerbated by
  d. Certainty of the relationship
  e. Often related to
K. Severity relative to other problems
L. Relationship to "routine" problem set patterns ODL. in one embodiment, patients and their providers can be surveyed for candidate activities of daily living that correlate with quality of life to determine which ODL information 220 is relevant to MD populations. The ODL information 220 (as well as the device information 205, the medical record information 245, and any other information) can also be created, entered, and/or saved using problem-oriented medical records so that it can be correlated with the PCHR information 205. A data collection tool set can be created which allows patients and families to collect ODL data regardless of technological access or expertise. In addition, a problem-oriented user interface can be built, rich in problem metadata that allows patients to view and document their current condition(s) and understand their responses to therapies.

In one embodiment, a user can log into a system and see a home screen. Then a problem list can be illustrated to provide a visual representation of the patients problems. This can include a written and/or graphical depiction of the current status of the patient's problems, including: how the various problems are interrelated; the category of each problem (e.g., acute, chronic, allergies, family history, past medical history, etc.); the urgency/priority of each problem; or the degree of precision/substantiation/understanding of the problem, or any combination thereof.

Figure 3:
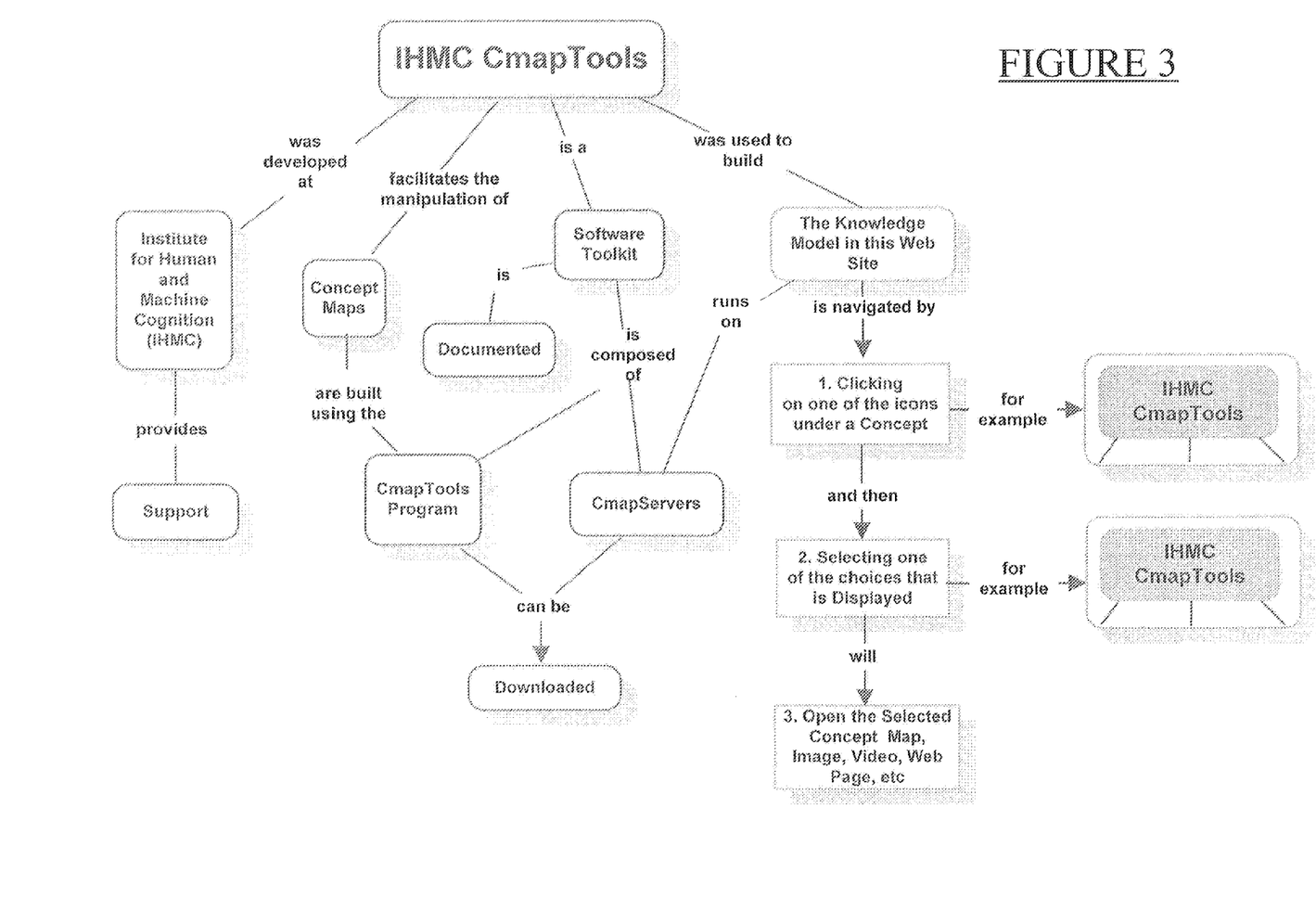
FIG. 3 illustrates an example of a mindmap, according to an embodiment.

In one embodiment, the user can have the ability to drill down into a problem to see the substantiating information and the history of the problem and how it is being managed. In one embodiment, a mindmap style graphical user interface (GUI) can be utilized. FIG. 3 illustrates an example of a mindmap, where a diagram can be used to represent words, ideas, tasks, or other items linked to and arranged around a central key word or idea. Mind maps can be used to generate, visualize, structure, and classify ideas, and aid in study, organization, problem solving, decision making, and writing. Thus, for example, the user can use a mindmap similar to the one illustrated in FIG. 3 to add a new problem, re-parent existing problems, set relationships between problems, and set relationships between problems and observations. In addition, multiple parents can be used for a given problem.

In one embodiment, observations can be viewed (e.g., by a doctor, service provider, patient, family member). For example, observations related to vital signs, lab results, consult results, imaging or pathology interpretations can be assessed and conclusions reported to the client. New observations can be pointed out. In addition, problems can be suggested.

In one embodiment, a presentation of the patient's problems over time (e.g., days, months, years, lifetime) can be illustrated. This can allow efficient viewing of the patient's problems over a timeline to help provide information about a particular encounter and when it happened in the past. An overview can be provided, with the ability to drill down where needed to obtain details.

In one embodiment, a hand-over tool can be provided. This can be a complete and current status of the patient. It can be used to facilitate hand-over of care from one provider to another. Daily progress notes can be created and automated with content and structure identical or coordinating with that of the hand-over content. Text can be included describing: new problems, resolution of former problems, how problems are linked, how problems were updated when new encounter findings arrived, etc. If something is changed in the hand-over tool, this can be reflected in what is used by the client, as well as all pieces of the tool.

Using the muscular dystrophy example, the metadata extensions in the UMLS semantic network can help make the functionality for a muscular dystrophy focused PCHR viable. It is insufficient to know a patient has the problem "abdominal pain." The pain may likely have an imprecisely known onset. The pain may be possibly associated with a number of conditions (e.g., duodenal ulcer, kidney stone, viral gastroenteritis). In turn, each condition can be associated with a likelihood based on other patient characteristics or characteristics within a subpopulation of similar patients. The problem may be resolved within a precisely known date or may "morph" into right lower lobe pneumonia. The subsequent resolution may be associated with a specific therapy.

With a rich problem-oriented metadata structure, the PCHR information 205 can allow automated learning for this specific patient when the abdominal pain returns and memories of the original episode have faded. Further, other patients with a similar conditions and problem patterns can begin to benefit from the experience of others. Best practice will evolve not only from the selected patient populations of university investigators but also from the individual experiences of all patients with muscular dystrophy who maintain PCHR information 205 and who specifically choose to contribute their information to the community. The medical problems can include symptoms, signs, diagnosis, problem prevention, or other data. The problems can be variably organized (e.g., organ system, time, degree of certainty). The medical problems can include information from various sources (e.g., home, rehabilitation center, doctor's office, acute facility, critical care facility).

Utilizing The Information. Once the problem-oriented medical records are created, they can be utilized with the PCHR information 205, the device information 210, the ODL information 220, the medical records information 245, and other information to share information and perform problem-based pattern matching. In this manner, many functions (e.g., medical data input, storage, aggregation, retrieval, display) can be performed utilizing this problem information. Patterns can be identified, problems can be documented, decision support tools can be interacted with, and the patient can be treated and communicated with by utilizing the problem-focused data. Decision support can then be delivered in a problem-oriented fashion.

FIG. 5 illustrates an example of cognitive activity pattern recognition. In this example, patterns can be seen as templates or a merger of template fragments. Situation analysis can be done on a strategic level by physicians or on a tactical level by a family member/friend or house staff. Uncertainty can be managed by gaining more information (e.g., examining a patient's response), narrowing diagnostic options/possibilities, using differing organization to make sense of patient data (e.g., an organ view v. a problem view), or tolerating the uncertainty for a period of time until new or different data is available. Team coordination in this example includes team communication, fragmentary teams, shifting teams, shift hand-offs, role ambiguity, and external collaborators.

Problem-based pattern matching can help patterns of care to be identified and also help establish evidence-based practices across populations of similar patients. In addition, cross-patient analysis can be supported. Furthermore, a comparison of one patient's cluster of problems to another can be done so similar patients can be identified to facilitate decisions.

The PCHR information 205 can be organized by clinical problem, associated therapies, and/or outcomes (or any combination thereof) to create a consistent and comprehensive story about how patients manage their problems. This story can include information from home intensive care environments. With the documentation of ODL information 220, patients and providers can have a more comprehensive view of each patient's reality. This can help make the PCHR information 205 an effective data tool to communicate salient information to providers and thus allow a patient/family to be a full partner in their health and disease management.

The PCHR information 205 can increase communication between doctors and providers. It can also allow extension of the patient communities that connect patients with similar conditions. Completely at the discretion of the patient, researchers could find people with similar conditions and compare care and therapies. Further, patients could elect to either broadcast to authorized researchers their condition patterns or ask researchers to send them condition patterns the researchers wish to study. Patients need not identify themselves to the research until after they approve the study or desire more information. This can vastly increase the data available for research and decrease expenses and time involved with data collection.

Examples of the type of information that can be generated and utilized using the problem-oriented data include the following:

1. Problems can be displayed on a timeline and temporal relationships between problems can be identifiable.

2. Decisions (e.g. diagnostic procedures or therapies) can be linked to a problem(s) so patient-centric responses to the decisions can be tracked.

3. Problems can be associated with specific primary data elements, and a patient's primary data elements can be routinely scanned for problem pattern matches.

4. Pattern matches can be ranked by likelihood based on the degree of fit with one specific problem and/or the likelihood of a proposed problem being found associated with other problems in a specific patient's profile.

5. Pattern matches can be stratified by the strength of each match. "Strength" can be assigned and displayed in multiple scales (e.g., specificity of data elements within single problem, strength of association of associated problems, and/or subjective scales of provider-specific intuition).

6. Multiple problems can be suggested to be related and unified within a "larger" single problem.

7. Multiple problems can be found to be related to a "higher" single problem.

8. A particular patient's pattern of problems can be compared to patterns from other patients so "nearest neighbor" analyses can be done.

9. Based on the "nearest neighbor" analyses, aggregation of a patient's specific nearest neighbors can allow for the prediction of a recovery trajectory.

10. Physician documentation can be aggregated in a problem-oriented structure.

11. With problem-oriented records, multiple services can be documented in the same place.

12. Situational awareness can be better and faster than in a current scattered paper-based and/or electronic health records.

13. Monitoring of observations that have changed and an indication of what associated problems need to be re-evaluated can be automated and better utilized. For example, as new observations arrive: problems linked to a previous observation(s) can be displayed as needing reassessment; "textbook" problems driven "by definition" from lab results can be automatically suggested to the user; and/or second degree problems derived by consulting the problem knowledge base can be suggested.

14. Prompting can be done for problems that can be derived from key laboratory results (e.g., hypokalemia).

For example, children with muscular dystrophies (MD) have heterogeneous diseases and myriad phenotypes within a single genotype. Manifestations range from exercise intolerance and muscle pain manifesting in adults to respiratory failure beginning in childhood. A particularly vulnerable subset of children and adults with MD are those requiring home-based mechanical ventilation. The home-based system is a complex set of life saving therapies including a ventilator, a back-up ventilator, oxygen, suction equipment and physiologic monitors. Local practice guidelines exist to manage ventilator-dependant patients in the home environment. If consistent and reliable data can be collected from home, the extent guidelines are followed and the effectiveness of the guidelines can be tracked and used to better treat patients. In addition, if information can be compiled from multiple parties and made available to multiple parties, care can be coordinated between the home, rehabilitation, acute, and/or critical care facilities.

Once the data is collected, it can be analyzed from physiological monitors, medical devices, and ODL information 220 to discover patterns in home therapy treatments and draw conclusions about current therapies. Patterns of data can be identified that flag clinically significant events and trends requiring immediate intervention. In addition, patterns of data can be identified that suggest improvements in conditions that warrant analysis and knowledge transfer to the wider muscular dystrophy communities.

Physicians can use various methods to discover information about a patient. Such methods are usually not followed in the out-patient environments, in the home, and certainly not by the patient or their family providers. An medical-specific PCHR can be built using an existing open-source solution (Indivo) to aggregate information from medical monitors and device, ODLs, and standard medical data from hospital information systems. One example of a PCHR upon which this project can be built is Indivo (Simons, Mandl, & Kohane, 2005) and maintained within the Children's Hospital informatics Program in Boston. Indivo is an open source, open standards PCHR with an open application programming interface (API). The Privacy and Security Rules of the Health Insurance Portability and Accountability Act (HIPAA) are exceeded.

The Indivo server is a middle layer and is responsible for managing not content but rather integration and security services. (See FIG. 6 for an example of how an Indivo server could work with PCHR information 205). The Indivo server 605 can be connected to an encrypted data store 610 and the API 615. There can be multiple user interfaces to facilitate users 625, data providers 630, and services 635 so that patients with different diseases and other characteristics can have all relevant information utilized. All communication in the Indivo system can use standard web protocols. Indivo can working closely with standards organizations such as Health Information Technology Standards Panel. Standard coding systems (e.g. LOINC and SNOMED) may be used when the source data provider supports them.

Figure 6:
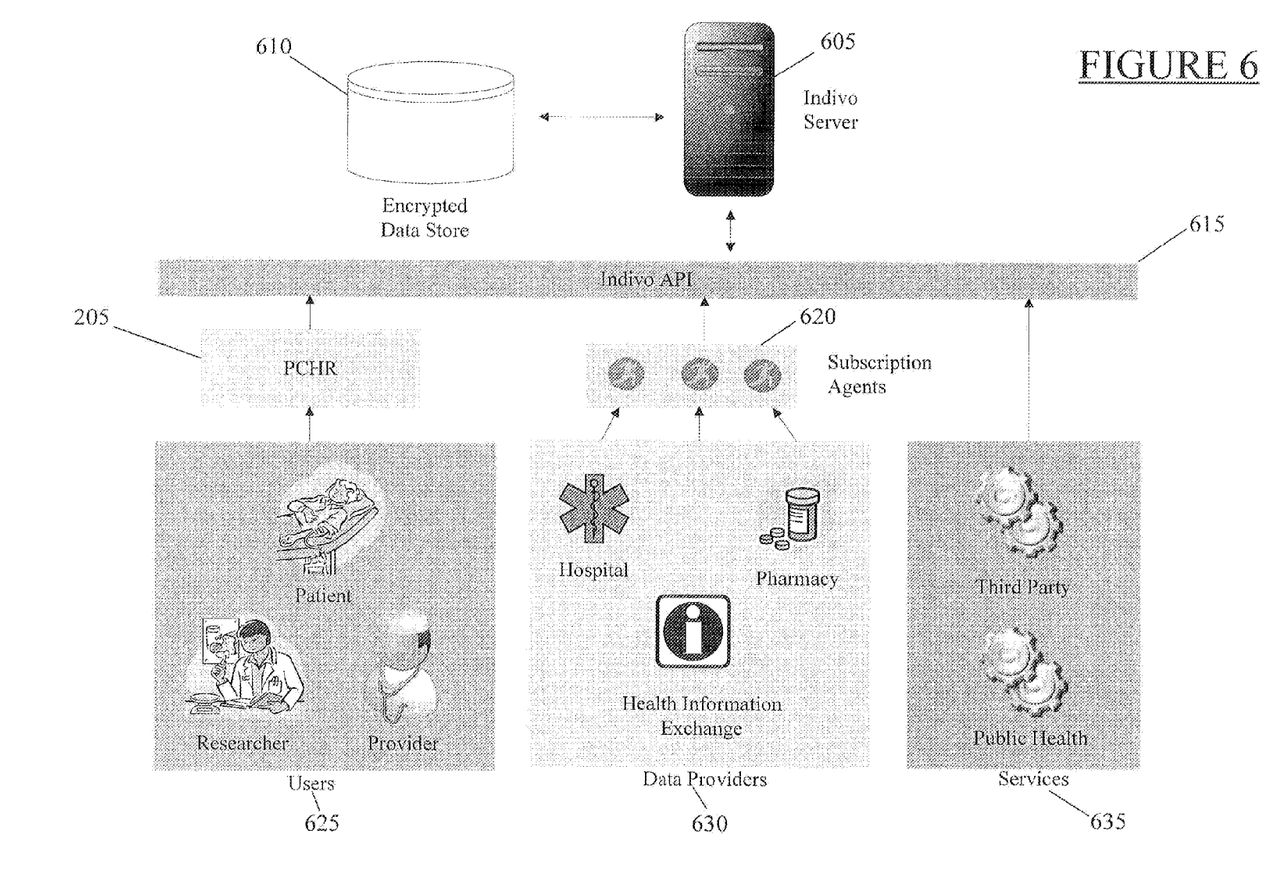
FIG. 6 illustrates an example of how an Indivo server may work with personally controlled health record (PCHR) information, according to an embodiment.

Personal Health Records (PHRs) (e.g., from Microsoft, Google, Dossia), through the Indivo API 615 can, with the patient's approval, get to the patient PCHR information 205 through the Indivo server 605. (Indivo is open source.) This interoperability can be helpful for patients as they move between health plans or employers, and will be driven by consumer demand.

Cardiopulmonary Corporation, for example, can provide the connection hubs, interfaces to the medical devices and interfaces to the HealthVault using Bernoulli® Enterprise Monitoring clinical monitoring solution, which is commercially available and has received 510(k) clearance from the United States Food and Drug Administration. In one embodiment, this application could be the central monitoring station.

In one embodiment, observations of daily living (ODLs) from, for example, 50 children with rheumatologic diseases, including 26 pediatric SLE patients from The Johns Hopkins Children's Center (JHCC), can be entered into a secure server that can be accessed on the Internet. The project can link the ODLs with data from periodic physical examinations findings, vital signs, medical device data, laboratory data and text documents and therapy data. The ODLs can be juxtaposed with treatment and progression to elucidate the correlations between the ODLs and therapy in real time.

Constant updates of the patient's ODLs can have an impact on the treatment the providers can offer. Self-reporting of fatigue and irritability could be subtle central nervous system (CNS) signs and reveal early signs of NPSLE. Pain scores could be useful for assessing the arthritis. Reports from home scales of weight gain or other such side effects could reveal issues with medication. Wearable sensors such as accelerometry, pedometry, and heart rate data could send data back to the secure server and enable a more passive collection of ODLs. Providers could offer treatment to tackle problems based on everyday observations rather than waiting for the patient's visit to the hospital.

Patients of any IT sophistication can access and/or utilize the information sharing application 120. For example, some patients have no access to IT. They could work with a data counselor, a trusted guardian of the patient's data and access. This group could be asked to keep a small notebook of their ODLs. The notebook forms could be patterned after their automated counterparts and could include both checklists and text entry. On a weekly basis, the patients could meet with the data counselor to submit the ODLs for the counselor to enter them into the database. The patient could receive any automated alerts based on their ODLs from the previous week. The patient could view or receive a print out of the activity on the rheumatologic diseases community chat boards.

Some patients have limited access or knowledge of IT. Patients in this category could have access to cellular telephones and text messages but with more limited access to computers. Patients could therefore text their ODLs to a database where they would be collected by the data counselor and uploaded onto their personal website. For example, a patient page could be populated by cell phone text pages. When they do access a computer, their website would appear with all their properly organized updates from their cellular phones.

Other patients have good access to IT and could be given a tutorial as to how the website and text messaging service works. After the tutorial, this group may not regularly involve the data counselor.

Figure 7:
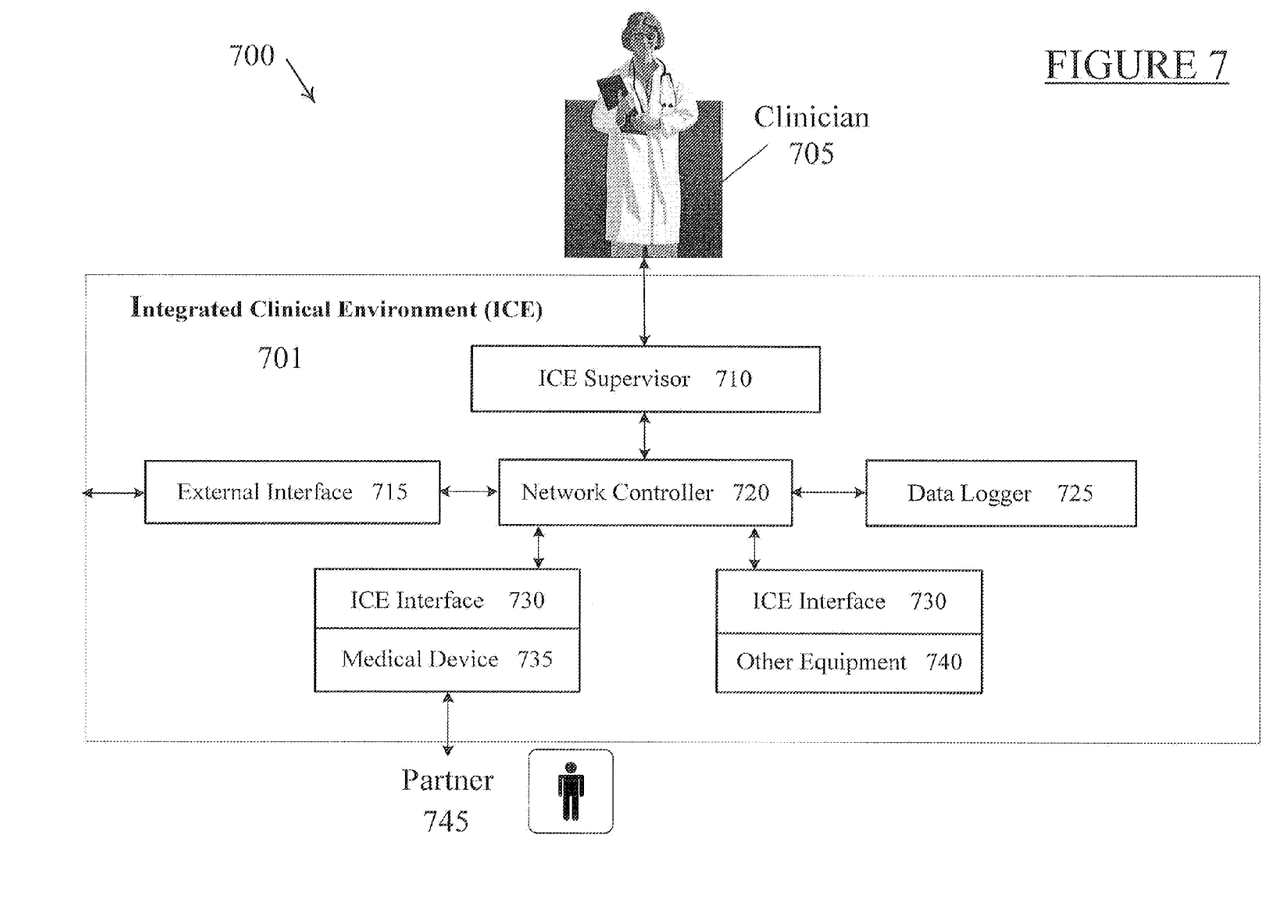
FIG. 7 illustrates an example screen for a data counselor or provider who handles multiple patients, according to an embodiment.

FIG. 7 shows an example screen for a data counselor or provider who handles multiple patients. The clinician 705 can access an integrated clinical environment (ICE) application 701 through an ICE supervisor 710 to access at least one external interface 715, at least one network controller 720, and at least one data logger 725. The partner 745 can also access the ICE 700 (using, for example, at least one medical device 735 or other equipment 740) through an ICE interface 730.

Utilizing some or all of the above features, the information sharing application 120 can help deconstruct physician care for hospitalized patients, analyze the component physical and cognitive tasks, redistribute the tasks to physician team members with the appropriate skill set (and likely to non-physicians), and reconstruct an innovative physician team. Commonalities across multiple venues (e.g. intensive care and "ward" care) and services (e.g. pediatrics, internal medicine, surgery) can be sought.

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above-described embodiments.

In addition, it should be understood that any figures which highlight the functionality and advantages, are presented for example purposes only. The disclosed methodology and system are each sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

In addition, it is the applicant's intent that when an element of the system or method is described as "an" element, it is meant to include "at least one" of that element. For example, if "a" learning engine is described, "at least one" learning engine is also meant to be described.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A computer method for sharing medical information, comprising:
    performing processing associated with creating, utilizing at least one information sharing application in communication with at least one client computer and/or at least one server computer, a plurality of relational problem-oriented records utilizing at least one problem pattern for each of a plurality of medical problems, wherein each of the plurality of relational problem-oriented records comprises relationship information for each of the plurality of medical problems, wherein the relationship information comprises: at least one other medical problem caused by at least one medical problem, or at least one other medical problem that is a result of the at least one medical problem, or at least one other medical problem exacerbated by the at least one medical problem, or at least one other medical problem often related to the at least one medical problem, or any combination thereof;
    performing processing associated with organizing at least two of the plurality of relational problem-oriented records, utilizing the at least one information sharing application in communication with at least one client computer and/or at least one server computer, wherein the organizing comprises matching at least one problem pattern in at least two relational problem-oriented records; and
    performing processing associated with sharing information related to at least one of the at least two relational problem-oriented records from the at least one information sharing application with at least one user utilizing at least one client computer and/or at least one server computer, wherein the sharing comprises searching at least two organized relational problem-oriented records for at least one problem pattern and making, available search results to the at least one user.

2. The method of claim 1, wherein problem-based pattern matching is performed utilizing, the plurality of relational problem-oriented records.

3. The method of claim 1, wherein the information is utilized by at least one provider and/or at least one medical patient.

4. The method of claim 1, wherein at least one user utilizes the at least one information sharing application to indicate at least one reason why at least one problem is created, resolved and/or prioritized.

5. The method of claim 1, wherein the at least one information sharing application alerts at least one user when new information is available of interest to the at least one user.

6. The method of claim 1, wherein the at least one sharing application shares the following information between users: medical record information, or device information, or observations of daily living (ODL) information, or any combination thereof.

7. A computerized system for sharing medical information, comprising:
    at least one server computer and/or at least one client computer coupled to a network;
    at least one application coupled to the at least one server computer and/or the at least one client computer, the at least one application configured for:
    performing processing associated with creating, utilizing at least one information sharing application in communication with at least one client computer and/or at least one server computer, a plurality of relational problem-oriented records utilizing at least one problem pattern for each of a plurality of medical problems, wherein each of the plurality of relational problem-oriented records comprises relationship information for each of the plurality of medical problems, wherein the relationship information comprises: at least one other medical problem caused by at least one medical problem, or at least one other medical problem that is a result of the at least one medical problem, or at least one other medical problem exacerbated by the at least one medical problem, or at least one other medical problem often related to the at least one medical problem, or any combination thereof;
    performing processing associated with organizing at least two of the plurality of relational problem-oriented records, utilizing the at least one information sharing application in communication with at least one client computer and/or at least one server computer, wherein the organizing comprises matching at least one problem pattern in at least two relational problem-oriented records; and performing processing associated with sharing information related to at least one of the at least two relational problem-oriented records from the at least one information sharing application with at least one user utilizing at least one client computer and/or at least one server computer, wherein the sharing comprises searching at least two organized relational problem-oriented records for at least one problem pattern and making available search results to the at least one user.

8. The system of claim 7, wherein problem-based pattern matching is performed utilizing the plurality of problem-oriented records.

9. The system of claim 7, wherein the information is utilized by at least one provider and/or at least one medical patient.

10. The system of claim 7, wherein at least one user utilizes the at least one information sharing application to indicate at least one reason why at least one problem is created, resolved and/or prioritized.

11. The system of claim 7, wherein the at least one information sharing application alerts at least one user when new information is available of interest to the at least one user.

12. The system of claim 7, wherein the at least one sharing application shares the following information between users: medical record information, or device information, or observations of daily living (ODL) information, or any combination thereof.

13. The method of claim 1, wherein the relationships further comprise; a certainty of the relationship, or the severity of the problem relative to the severity of another problem, or how the problem relates to a routine problem set pattern of another problem, or any combination thereof.

14. The system of claim 7, wherein the relationships further comprise; a certainty of the relationship, or the severity of the problem relative to the severity of another problem, or how the problem relates to a routine problem set pattern of another problem, or any combination thereof.

15. The method of claim 1, wherein the at least one organized problem pattern utilizes preset list criteria.

16. The system of claim 7, wherein the at least one organized problem pattern utilizes preset list criteria.

* * * * *

UNITED STATES PATENT AND TRADEMARK OFFICE
CERTIFICATE OF CORRECTION

PATENT NO. : 8,473,308 B2
APPLICATION NO. : 13/062631
DATED : June 25, 2013
INVENTOR(S) : Fackler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 112 days.

Signed and Sealed this
Eighth Day of September, 2015

Michelle K. Lee
*Director of the United States Patent and Trademark Office*